US012582398B2

(12) United States Patent
Weir et al.

(10) Patent No.: US 12,582,398 B2
(45) Date of Patent: *Mar. 24, 2026

(54) CARTRIDGE STATUS AND PRESENCE DETECTION

(71) Applicant: Intuitive Surgical Operations, Inc., Sunnyvale, CA (US)

(72) Inventors: David W. Weir, Emerald Hills, CA (US); Kevin Durant, Alameda, CA (US); William Burbank, Sandy Hook, CT (US); Patrick Flanagan, Santa Clara, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 110 days.

This patent is subject to a terminal disclaimer.

(21) Appl. No.: 18/488,496

(22) Filed: Oct. 17, 2023

(65) Prior Publication Data

US 2024/0041456 A1     Feb. 8, 2024

Related U.S. Application Data

(60) Continuation of application No. 17/066,110, filed on Oct. 8, 2020, now Pat. No. 11,812,921, which is a
(Continued)

(51) Int. Cl.
*A61B 17/072*        (2006.01)
*A61B 34/30*        (2016.01)
(Continued)

(52) U.S. Cl.
CPC ........ *A61B 17/07207* (2013.01); *A61B 34/30* (2016.02); *A61B 34/37* (2016.02);
(Continued)

(58) Field of Classification Search
CPC ........... A61B 2017/00039; A61B 2017/00398; A61B 2017/00477; A61B 2017/07271;
(Continued)

(56) References Cited

U.S. PATENT DOCUMENTS 6,849,071 B2 * 2/2005 Whitman ............... A61B 34/71
606/1
7,721,936 B2 * 5/2010 Shalton, IV ..... A61B 17/07207
227/176.1
(Continued)

FOREIGN PATENT DOCUMENTS

EP        0679367 A2    11/1995
EP        0552050 B1    5/2000
(Continued)

OTHER PUBLICATIONS

Extended European Search Report for Application No. EP16192108. 5, mailed on Mar. 23, 2017, 9 pages (ISRG03830D1/EP).
(Continued)

*Primary Examiner* — Veronica Martin
*Assistant Examiner* — Mary C Hibbert-Copeland
(74) *Attorney, Agent, or Firm* — Sheppard, Mullin, Richter & Hampton LLP; Xin Xie

(57)        ABSTRACT

Surgical systems and related methods for detecting whether a surgical instrument lacks a surgical cartridge in an unfired condition. A method of detecting that a surgical instrument lacks a surgical cartridge in an unfired condition mounted to the surgical instrument includes commanding a movement of the actuation output in a direction opposite to a firing direction for the surgical cartridge, detecting that an actuation amount of the actuation output as a result of the commanded movement is at or above a threshold actuation amount, and in response to detecting that the actuation amount of the actuation output is at or above the threshold
(Continued)

actuation amount, determining that the surgical instrument lacks a surgical cartridge in the unfired condition mounted to the surgical instrument.

14 Claims, 10 Drawing Sheets

Related U.S. Application Data division of application No. 13/662,385, filed on Oct. 26, 2012, now Pat. No. 10,828,030.

(60) Provisional application No. 61/560,213, filed on Nov. 15, 2011, provisional application No. 61/551,880, filed on Oct. 26, 2011.

(51) Int. Cl.

| | |
|---|---|
| *A61B 34/37* | (2016.01) |
| *A61B 50/13* | (2016.01) |
| *A61B 17/00* | (2006.01) |
| *A61B 90/00* | (2016.01) |

(52) U.S. Cl.

CPC .... *A61B 50/13* (2016.02); *A61B 2017/00039* (2013.01); *A61B 2017/00398* (2013.01); *A61B 2017/00477* (2013.01); *A61B 2017/07271* (2013.01); *A61B 2017/07285* (2013.01); *A61B 2090/0804* (2016.02); *A61B 2090/0808* (2016.02)

(58) Field of Classification Search

CPC .. A61B 2017/07285; A61B 2090/0804; A61B 2090/0808; A61B 50/13; A61B 34/30; A61B 34/37; A61B 17/07207

USPC ...................................................... 227/180.1

See application file for complete search history.

(56) References Cited

U.S. PATENT DOCUMENTS

| | | | |
|---|---|---|---|
| 7,843,158 | B2 | 11/2010 | Prisco |
| 7,845,537 | B2 | 12/2010 | Shelton, IV et al. |
| 10,828,030 | B2 * | 11/2020 | Weir ...................... A61B 50/13 |
| 11,812,921 | B2 * | 11/2023 | Weir ................ A61B 17/07207 |
| 2004/0094597 | A1 | 5/2004 | Whitman et al. |
| 2008/0300580 | A1 | 12/2008 | Shelton, IV et al. |
| 2009/0289096 | A1 | 11/2009 | Shelton, IV et al. |
| 2010/0301095 | A1 * | 12/2010 | Shelton, IV ......... A61B 17/068 227/175.4 |
| 2011/0006103 | A1 | 1/2011 | Laurent et al. |
| 2011/0118778 | A1 | 5/2011 | Burbank |
| 2011/0174862 | A1 | 7/2011 | Shelton, IV et al. |
| 2012/0248167 | A1 * | 10/2012 | Flanagan ............. A61B 17/068 227/2 |
| 2021/0022738 | A1 | 1/2021 | Weir et al. |

FOREIGN PATENT DOCUMENTS

| | | | |
|---|---|---|---|
| EP | 1990015 | A2 | 11/2008 |
| EP | 2090255 | A1 | 8/2009 |
| EP | 2356949 | A2 | 8/2011 |
| JP | H067357 | A | 1/1994 |
| JP | 3532542 | B2 | 5/2004 |
| JP | 2004514490 | A | 5/2004 |
| JP | 2006034979 | A | 2/2006 |
| JP | 2007216012 | A | 8/2007 |
| JP | 2008212639 | A | 9/2008 |
| JP | 2009189841 | A | 8/2009 |
| JP | 2009202002 | A | 9/2009 |
| JP | 2010253272 | A | 11/2010 |
| WO | WO-2013063523 | A1 | 5/2013 |

OTHER PUBLICATIONS

Extended European Search Report for Application No. EP18215881. 6, mailed on Apr. 30, 2019, 9 pages (ISRG03830D2/EP).

Extended European Search Report for Application No. EP20120843240, mailed on Jul. 17, 2015, 7 pages (ISRG03830/EP).

International Search Report and Written Opinion for Application No. PCT/US2012/062299, mailed on Mar. 29, 2013, 11 pages.

Vertut, J., and Coiffet, P., "Robot Technology: Teleoperation and Robotics Evolution and Development." English translation, Prentice-Hall, Inc., Inglewood Cliffs, NJ, USA 1986, vol. 3A, 332 pages.

* cited by examiner

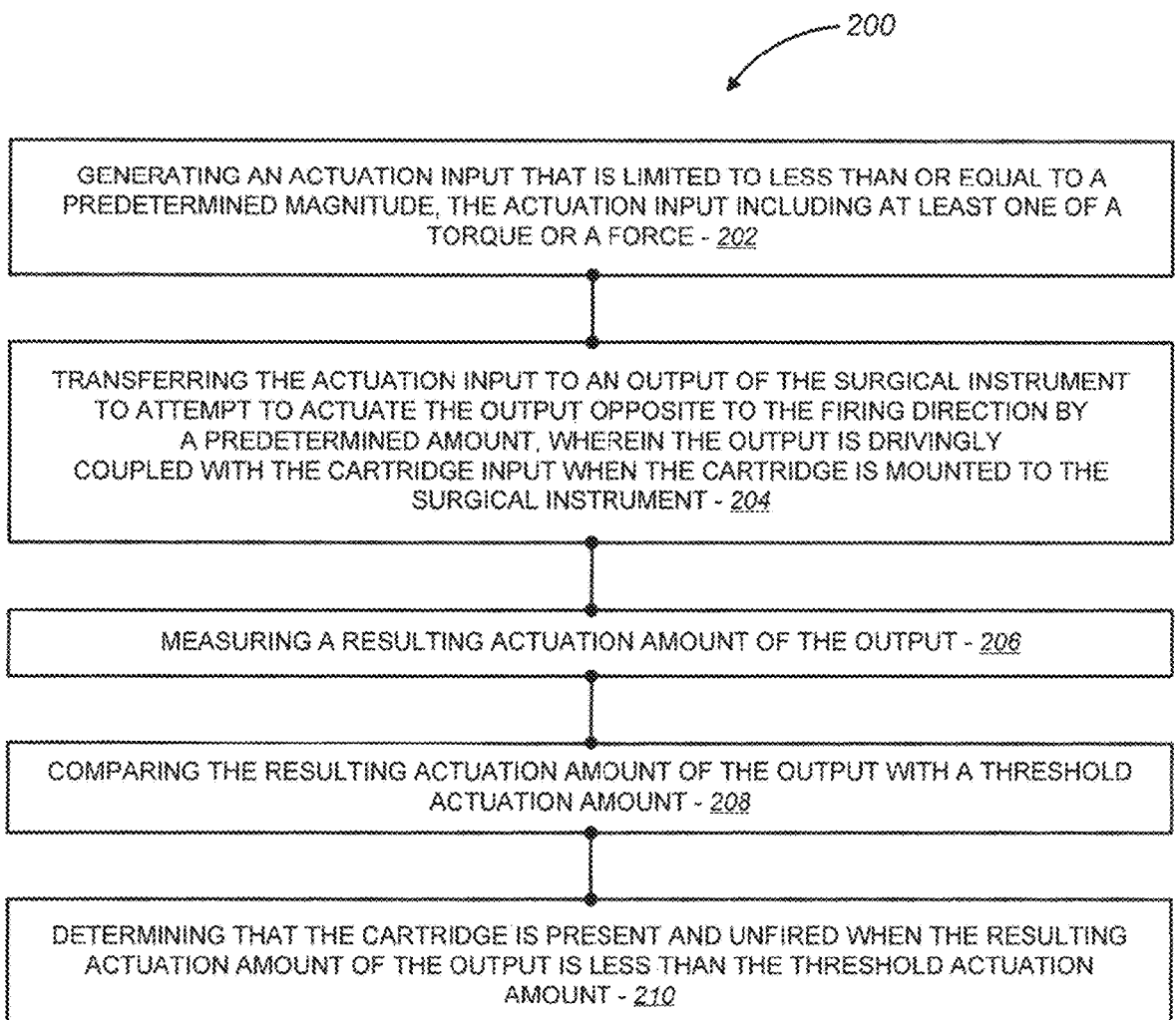

*200*

GENERATING AN ACTUATION INPUT THAT IS LIMITED TO LESS THAN OR EQUAL TO A PREDETERMINED MAGNITUDE, THE ACTUATION INPUT INCLUDING AT LEAST ONE OF A TORQUE OR A FORCE - *202*

TRANSFERRING THE ACTUATION INPUT TO AN OUTPUT OF THE SURGICAL INSTRUMENT TO ATTEMPT TO ACTUATE THE OUTPUT OPPOSITE TO THE FIRING DIRECTION BY A PREDETERMINED AMOUNT, WHEREIN THE OUTPUT IS DRIVINGLY COUPLED WITH THE CARTRIDGE INPUT WHEN THE CARTRIDGE IS MOUNTED TO THE SURGICAL INSTRUMENT - *204*

MEASURING A RESULTING ACTUATION AMOUNT OF THE OUTPUT - *206*

COMPARING THE RESULTING ACTUATION AMOUNT OF THE OUTPUT WITH A THRESHOLD ACTUATION AMOUNT - *208*

DETERMINING THAT THE CARTRIDGE IS PRESENT AND UNFIRED WHEN THE RESULTING ACTUATION AMOUNT OF THE OUTPUT IS LESS THAN THE THRESHOLD ACTUATION AMOUNT - *210*

*FIG. 10*

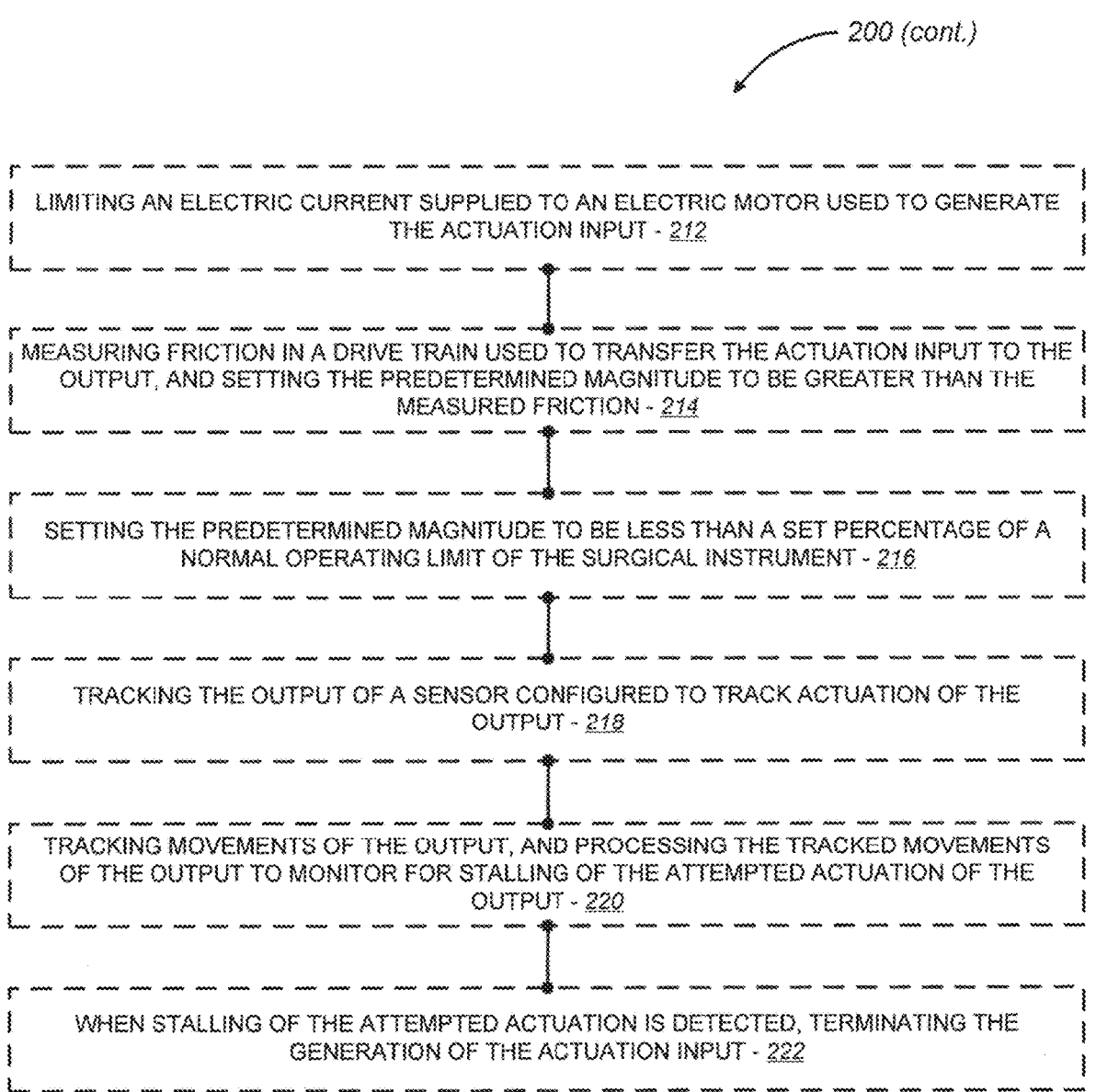

*200 (cont.)*

LIMITING AN ELECTRIC CURRENT SUPPLIED TO AN ELECTRIC MOTOR USED TO GENERATE THE ACTUATION INPUT - *212*

MEASURING FRICTION IN A DRIVE TRAIN USED TO TRANSFER THE ACTUATION INPUT TO THE OUTPUT, AND SETTING THE PREDETERMINED MAGNITUDE TO BE GREATER THAN THE MEASURED FRICTION - *214*

SETTING THE PREDETERMINED MAGNITUDE TO BE LESS THAN A SET PERCENTAGE OF A NORMAL OPERATING LIMIT OF THE SURGICAL INSTRUMENT - *216*

TRACKING THE OUTPUT OF A SENSOR CONFIGURED TO TRACK ACTUATION OF THE OUTPUT - *218*

TRACKING MOVEMENTS OF THE OUTPUT, AND PROCESSING THE TRACKED MOVEMENTS OF THE OUTPUT TO MONITOR FOR STALLING OF THE ATTEMPTED ACTUATION OF THE OUTPUT - *220*

WHEN STALLING OF THE ATTEMPTED ACTUATION IS DETECTED, TERMINATING THE GENERATION OF THE ACTUATION INPUT - *222*

*FIG. 11*

CARTRIDGE STATUS AND PRESENCE DETECTION

CROSS REFERENCE TO RELATED APPLICATION DATA

The present application is a Continuation of U.S. patent application Ser. No. 17/066,110 filed Oct. 8, 2020 (Allowed); which is a Divisional of U.S. patent application Ser. No. 13/662,385 filed Oct. 26, 2012 (now U.S. Pat. No. 10,828,030); which claims the benefit of U.S. Provisional Appln Nos. 61/551,880 filed Oct. 26, 2011 and 61/560,213 filed Nov. 15, 2011; the full disclosures which are incorporated herein by reference in their entirety for all purposes.

BACKGROUND

Minimally invasive surgical techniques are aimed at reducing the amount of extraneous tissue that is damaged during diagnostic or surgical procedures, thereby reducing patient recovery time, discomfort, and deleterious side effects. As a consequence, the average length of a hospital stay for standard surgery may be shortened significantly using minimally invasive surgical techniques. Also, patient recovery times, patient discomfort, surgical side effects, and time away from work may also be reduced with minimally invasive surgery.

A common form of minimally invasive surgery is endoscopy, and a common form of endoscopy is laparoscopy, which is minimally invasive inspection and surgery inside the abdominal cavity. In standard laparoscopic surgery, a patient's abdomen is insufflated with gas, and cannula sleeves are passed through small (approximately one-half inch or less) incisions to provide entry ports for laparoscopic instruments.

Laparoscopic surgical instruments generally include an endoscope (e.g., laparoscope) for viewing the surgical field and tools for working at the surgical site. The working tools are typically similar to those used in conventional (open) surgery, except that the working end or end effector of each tool is separated from its handle by an extension tube (also known as, e.g., an instrument shaft or a main shaft). The end effector can include, for example, a clamp, grasper, scissor, stapler, cautery tool, linear cutter, or needle holder.

To perform surgical procedures, the surgeon passes working tools through cannula sleeves to an internal surgical site and manipulates them from outside the abdomen. The surgeon views the procedure from a monitor that displays an image of the surgical site taken from the endoscope. Similar endoscopic techniques are employed in, for example, arthroscopy, retroperitoneoscopy, pelviscopy, nephroscopy, cystoscopy, cisternoscopy, sinoscopy, hysteroscopy, urethroscopy, and the like.

Minimally invasive telesurgical robotic systems are being developed to increase a surgeon's dexterity when working on an internal surgical site, as well as to allow a surgeon to operate on a patient from a remote location (outside the sterile field). In a telesurgery system, the surgeon is often provided with an image of the surgical site at a control console. While viewing an image of the surgical site on a suitable viewer or display, the surgeon performs the surgical procedures on the patient by manipulating master input or control devices of the control console. Each of the master input devices controls the motion of a servo-mechanically actuated/articulated surgical instrument. During the surgical procedure, the telesurgical system can provide mechanical actuation and control of a variety of surgical instruments or tools having end effectors that perform various functions for the surgeon, for example, holding or driving a needle, grasping a blood vessel, dissecting tissue, or the like, in response to manipulation of the master input devices.

Manipulation and control of these end effectors is a particularly beneficial aspect of robotic surgical systems. For this reason, it is desirable to provide surgical tools that include mechanisms that provide three degrees of rotational movement of an end effector to mimic the natural action of a surgeon's wrist. Such mechanisms should be appropriately sized for use in a minimally invasive procedure and relatively simple in design to reduce possible points of failure. In addition, such mechanisms should provide an adequate range of motion to allow the end effector to be manipulated in a wide variety of positions.

Surgical clamping and cutting instruments (e.g., non-robotic linear clamping, stapling, and cutting devices, also known as surgical staplers; and electrosurgical vessel sealing devices) have been employed in many different surgical procedures. For example, a surgical stapler can be used to resect a cancerous or anomalous tissue from a gastro-intestinal tract. Many known surgical clamping and cutting instruments, including known surgical staplers, have opposing jaws that clamp tissue and an articulated knife to cut the clamped tissue.

Many surgical clamping and cutting instruments are configured to interact with a limited extent of patient tissue. For example, a surgical stapler is typically configured to clamp, staple, and cut a limited length of patient tissue, especially where the surgical stapler has a compact size suitable for deployment into a restrictive body cavity (e.g., through a cannula to inside the pelvis). The surgical procedure involved, however, can require the stapling of more than the limited length of patient tissue, thereby necessitating the use of another surgical stapler and/or the reloading of staples into the surgical stapler before it can be re-used. To facilitate re-use, many surgical staplers employ a stapler cartridge that is demountably attachable to an end effector jaw. Such stapler cartridges can include the required staples and a drive mechanism to deploy the staples and to articulate a knife to cut the stapled tissue. Following use, a spent stapler cartridge can be replaced with a new stapler cartridge and the surgical stapler re-used.

To reload a stapler cartridge in a laparoscopic surgical instrument, it is necessary to withdraw the surgical instrument from the surgical site and from the cannula. The removal is time consuming and delays the surgical procedure. As such, it is desirable that the instrument removal not occur when the surgical instrument has a cartridge that has not yet been fired. In a surgical procedure, however, it may occur that uncertainty exists regarding whether a particular surgical instrument has a spent cartridge or an unspent cartridge. Additionally, even when a surgical instrument is accessible to inspect the cartridge, it may not be readily apparent whether the cartridge is spent or unspent, especially to the untrained eye.

Thus, there is believed to be a need for a method to verify the presence of an unfired surgical cartridge mounted to a surgical instrument. Such a method should preferably be automated and able to be incorporated into a robotic surgical system used to manipulate the surgical instrument.

BRIEF SUMMARY

Surgical systems that automatically verify the presence of an unfired surgical cartridge mounted to a surgical instrument, and related methods, are disclosed. The disclosed methods attempt to drive an actuation output of the surgical instrument opposite to a firing direction of the cartridge by a predetermined amount. If the cartridge has been fired or is not present, the actuation output can be actuated by the predetermined amount. If an unfired surgical cartridge is present, the actuation output can only be actuated less than a threshold actuation amount before the attempted actuation stalls. The approach can be used to automatically verify the presence of an unfired surgical cartridge, thereby saving time and expense associated with manual verification and enabling verification of the presence of an unfired surgical cartridge mounted to a deployed surgical instrument without removing the surgical instrument from the surgical site. The approach can be used at any suitable time. For example, the approach can be used as an initial check. The approach can also be used on a periodic basis. The approach can also be used on a continual basis, such as by using a low actuation level (e.g., force and/or torque) and checking for movement.

Thus, in one aspect, a method is disclosed of verifying presence of an unfired surgical cartridge mounted to a surgical instrument. The cartridge includes an input that is actuated in a firing direction to operate the cartridge. The method includes generating an actuation input that is limited to less than or equal to a predetermined magnitude. The actuation input includes at least one of a torque or a force. The actuation input is transferred to an output of a surgical instrument to attempt to actuate the output opposite to the firing direction by a predetermined amount. The output is drivingly coupled with the cartridge input when the cartridge is mounted to the surgical instrument. The resulting actuation amount of the output is measured and compared with a threshold actuation amount. A determination is made that the cartridge is present and unfired when the resulting actuation amount of the output is less than the threshold actuation amount.

In many embodiments of the method, the actuation input is generated by an electric motor that is controlled to limit the actuation input generated. For example, the generation of the actuation input can include limiting an electric current supplied to the electric motor used to generate the actuation input.

The predetermined magnitude of the actuation input can be selected based on characteristics of a drive train used to transfer the actuation input to the surgical instrument output. For example, friction of the drive train used to transfer the actuation input to the output can be measured and the predetermined magnitude can be set to be greater than the measured friction.

In many embodiments of the method, the predetermined magnitude is set to be less than a normal operating limit of the surgical instrument. For example, in many embodiments the predetermined magnitude is set to be less than 40% of the normal operating limit of the surgical instrument. And in many embodiments, the predetermined magnitude is set to be less than 20% of the normal operating limit.

In many embodiments of the method, a sensor is used to measure the resulting actuation of the output. For example, a Hall sensor can be used to track actuation of a drive train used to transfer the actuation input to the surgical instrument output. As another example, an encoder can be used to track actuation of the drive train used to transfer the actuation input to the surgical instrument output. The actuation of the drive train can be tracked directly or indirectly by tracking the motion of an actuation source (e.g., a motor) that is drivingly coupled with the drive train.

In many embodiments of the method, movements of the output are tracked and processed to monitor for stalling of the attempted actuation of the output. When stalling of the attempted actuation is detected, the generation of the actuation input can be terminated.

In many embodiments of the method, the surgical cartridge includes an articulated knife. In many embodiments, the predetermined actuation amount is less than an amount that would result in exposure of the knife when applied to the surgical cartridge in a fired configuration.

In another aspect, a robotic surgical system is disclosed. The robotic surgical system includes a master input device, a surgical instrument including an actuation output, a robotic arm configured to move the surgical instrument in response to user manipulation of the master input device, a drive source drivingly coupled with the surgical instrument actuation output, a sensor configured to measure movement of the surgical instrument actuation output, and a controller communicatively coupled with the sensor and the drive source. The surgical instrument is configured to receive and support a surgical cartridge. The surgical cartridge includes an input that is actuated (e.g., rotated, translated) in a firing direction to operate the surgical cartridge. The cartridge is drivingly coupled with the actuation output when the surgical cartridge is mounted to the surgical instrument. The controller includes a processor and a tangible storage medium containing instructions that when executed cause the processor to control the drive source so that the drive source generates an actuation input that is less than or equal to a predetermined magnitude. The actuation input includes at least one of a torque or a force. The actuation input is transferred to the surgical instrument actuation output to attempt to move the actuation output opposite to the firing direction by a predetermined amount. The controller compares a resulting actuation amount of the actuation output with a threshold actuation amount and determines that the cartridge is present and unfired when the resulting actuation amount of the actuation output is less than the threshold actuation amount.

In many embodiments of the system, the actuation input is generated by an electric motor that is controlled to limit the actuation input generated. For example, the generation of the actuation input can include limiting an electric current supplied to the electric motor used to generate the actuation input.

In many embodiments of the system, the predetermined magnitude is set to be less than a normal operating limit of the surgical instrument. For example, in many embodiments the predetermined magnitude is set to be less than 40% of the normal operating limit of the surgical instrument. And in many embodiments, the predetermined magnitude is set to be less than 20% of the normal operating limit.

In many embodiments of the system, a sensor is used to measure the resulting actuation amount of the output. The controller can monitor an output signal of the sensor to determine if the resulting actuation amount of the actuation output is less than the threshold actuation amount. For example, the sensor can include a Hall sensor. The controller can count Hall sensor counts and compare the Hall sensor counts to a predetermined number to determine if the resulting actuation amount of the actuation output is less than the threshold actuation amount. As another example, an encoder can be used and an output signal of the encoder monitored by the controller to determine if the resulting actuation amount of the actuation output is less than the threshold actuation amount. As another example, the sensor can be a velocity sensor, such as an inductive velocity sensor or a tachometer. The controller can derive relative position from the measured velocity. As another example, the sensor can be an accelerometer, and position can be derived from the measured acceleration.

In many embodiments of the system, movements of the output are tracked to monitor for stalling of the attempted actuation. Stalling of the attempted actuation can be detected when the actuation output moves less than a minimum amount in a predetermined time period. When stalling of the attempted actuation is detected, the generation of the actuation input can be terminated.

In many embodiments of the system, the surgical cartridge includes an articulated knife. In many embodiments, the predetermined actuation amount is less than an amount that would result in exposure of the knife when applied to the surgical cartridge in a fired configuration. In many embodiments, the cartridge includes staples that are deployed into a clamped tissue when the cartridge is operated. In many embodiments, the articulated knife is configured to cut the clamped tissue between rows of the deployed staples. In many embodiments, the cartridge is configured to seal a vessel and includes an articulated knife configured to cut the sealed vessel.

For a fuller understanding of the nature and advantages of the present invention, reference should be made to the ensuing detailed description and accompanying drawings. Other aspects, objects and advantages of the invention will be apparent from the drawings and detailed description that follows.

BRIEF DESCRIPTION OF THE DRAWINGS

FIG. 10 lists acts of a method of verifying the presence of an unfired surgical cartridge mounted to a surgical instrument, in accordance with many embodiments.

FIG. 11 lists optional acts of the method of FIG. 10.

DETAILED DESCRIPTION

In the following description, various embodiments of the present invention will be described. For purposes of explanation, specific configurations and details are set forth in order to provide a thorough understanding of the embodiments. However, it will also be apparent to one skilled in the art that the present invention may be practiced without the specific details. Furthermore, well-known features may be omitted or simplified in order not to obscure the embodiment being described.

Minimally Invasive Robotic Surgery

Figure 1:
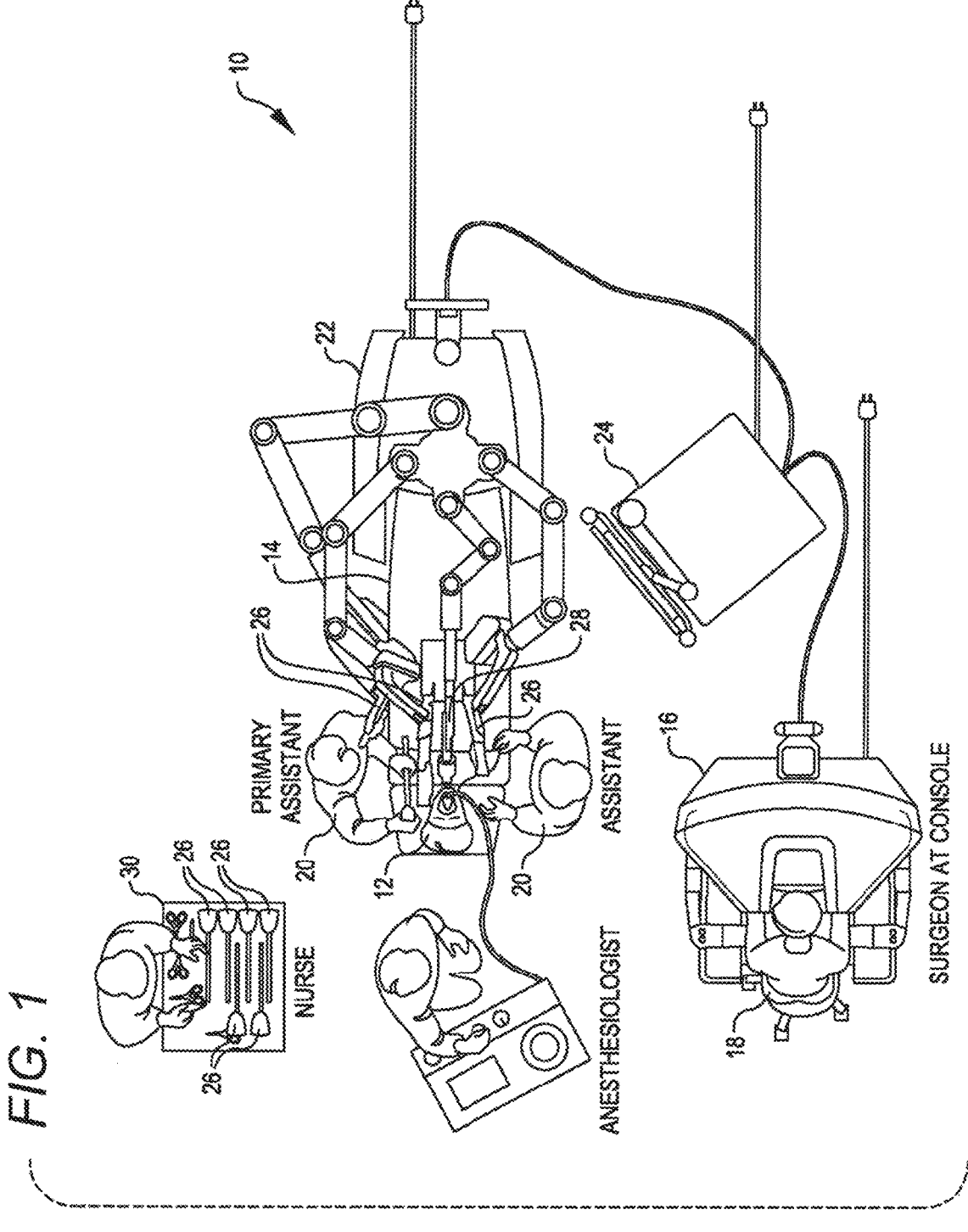
FIG. 1 is a plan view of a minimally invasive robotic surgery system being used to perform a surgery, in accordance with many embodiments.

Referring now to the drawings, in which like reference numerals represent like parts throughout the several views, FIG. 1 is a plan view illustration of a Minimally Invasive Robotic Surgical (MIRS) system 10, typically used for performing a minimally invasive diagnostic or surgical procedure on a Patient 12 who is lying down on an Operating table 14. The system can include a Surgeon's Console 16 for use by a Surgeon 18 during the procedure. One or more Assistants 20 may also participate in the procedure. The MIRS system 10 can further include a Patient Side Cart 22 (surgical robot) and an Electronics Cart 24. The Patient Side Cart 22 can manipulate at least one removably coupled tool assembly 26 (hereinafter simply referred to as a "tool") through a minimally invasive incision in the body of the Patient 12 while the Surgeon 18 views the surgical site through the Console 16. An image of the surgical site can be obtained by an endoscope 28, such as a stereoscopic endoscope, which can be manipulated by the Patient Side Cart 22 to orient the endoscope 28. The Electronics Cart 24 can be used to process the images of the surgical site for subsequent display to the Surgeon 18 through the Surgeon's Console 16. The number of surgical tools 26 used at one time will generally depend on the diagnostic or surgical procedure and the space constraints within the operating room among other factors. If it is necessary to change one or more of the tools 26 being used during a procedure, an Assistant 20 may remove the tool 26 from the Patient Side Cart 22, and replace it with another tool 26 from a tray 30 in the operating room.

Figures 2, 3:
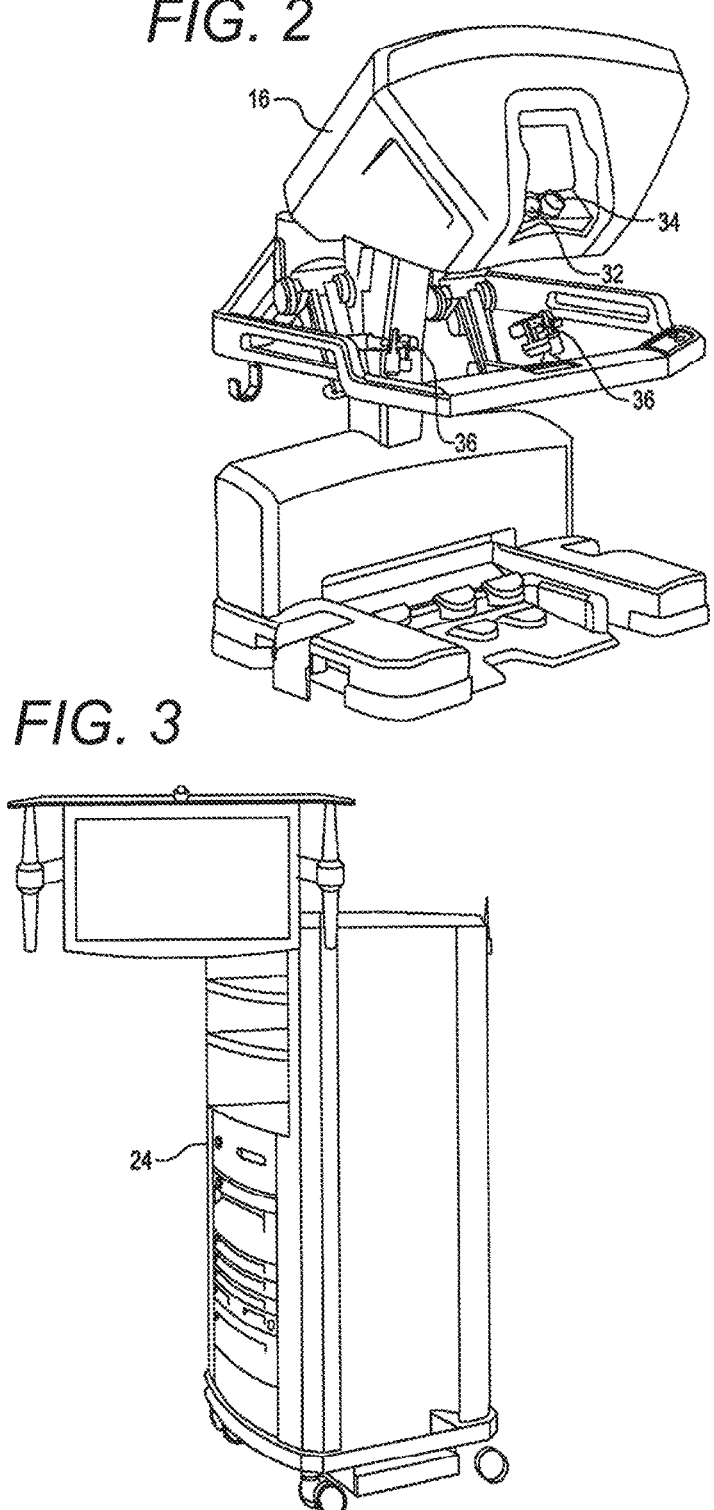
FIG. 2 is a perspective view of a surgeon's control console for a robotic surgery system, in accordance with many embodiments.
FIG. 3 is a perspective view of a robotic surgery system electronics cart, in accordance with many embodiments.

FIG. 2 is a perspective view of the Surgeon's Console 16. The Surgeon's Console 16 includes a left eye display 32 and a right eye display 34 for presenting the Surgeon 18 with a coordinated stereo view of the surgical site that enables depth perception. The Console 16 further includes one or more input control devices 36, which in turn cause the Patient Side Cart 22 (shown in FIG. 1) to manipulate one or more tools. The input control devices 36 can provide the same degrees of freedom as their associated tools 26 (shown in FIG. 1) to provide the Surgeon with telepresence, or the perception that the input control devices 36 are integral with the tools 26 so that the Surgeon has a strong sense of directly controlling the tools 26. To this end, position, force, and tactile feedback sensors (not shown) may be employed to transmit position, force, and tactile sensations from the tools 26 back to the Surgeon's hands through the input control devices 36.

The Surgeon's Console 16 is usually located in the same room as the patient so that the Surgeon may directly monitor the procedure, be physically present if necessary, and speak to an Assistant directly rather than over the telephone or other communication medium. However, the Surgeon can be located in a different room, a completely different building, or other remote location from the Patient allowing for remote surgical procedures.

FIG. 3 is a perspective view of the Electronics Cart 24. The Electronics Cart 24 can be coupled with the endoscope 28 and can include a processor to process captured images for subsequent display, such as to a Surgeon on the Surgeon's Console, or on another suitable display located locally and/or remotely. For example, where a stereoscopic endoscope is used, the Electronics Cart 24 can process the captured images to present the Surgeon with coordinated stereo images of the surgical site. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations.

Figure 4:
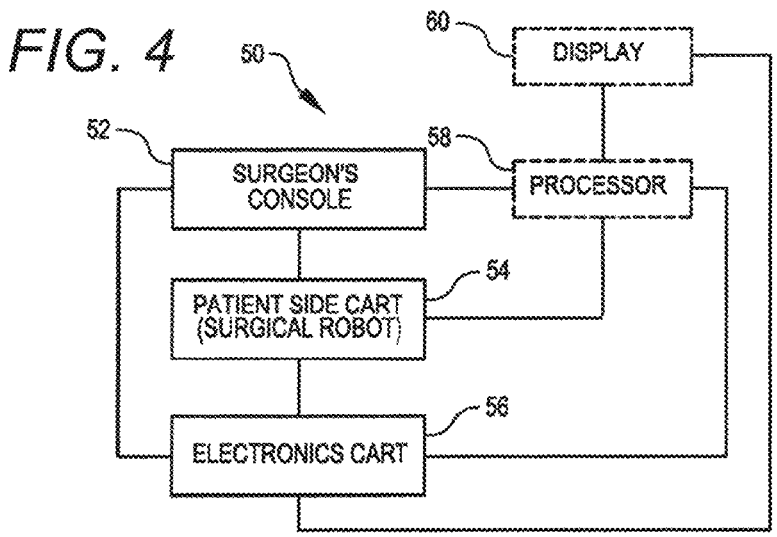
FIG. 4 diagrammatically illustrates a robotic surgery system, in accordance with many embodiments.

FIG. 4 diagrammatically illustrates a robotic surgery system 50 (such as MIRS system 10 of FIG. 1). As discussed above, a Surgeon's Console 52 (such as Surgeon's Console 16 in FIG. 1) can be used by a Surgeon to control a Patient Side Cart (Surgical Robot) 54 (such as Patient Side Cart 22 in FIG. 1) during a minimally invasive procedure. The Patient Side Cart 54 can use an imaging device, such as a stereoscopic endoscope, to capture images of the procedure site and output the captured images to an Electronics Cart 56 (such as the Electronics Cart 24 in FIG. 1). As discussed above, the Electronics Cart 56 can process the captured images in a variety of ways prior to any subsequent display. For example, the Electronics Cart 56 can overlay the captured images with a virtual control interface prior to displaying the combined images to the Surgeon via the Surgeon's Console 52. The Patient Side Cart 54 can output the captured images for processing outside the Electronics Cart 56. For example, the Patient Side Cart 54 can output the captured images to a processor 58, which can be used to process the captured images. The images can also be processed by a combination the Electronics Cart 56 and the processor 58, which can be coupled together to process the captured images jointly, sequentially, and/or combinations thereof. One or more separate displays 60 can also be coupled with the processor 58 and/or the Electronics Cart 56 for local and/or remote display of images, such as images of the procedure site, or other related images.

Figure 5A:
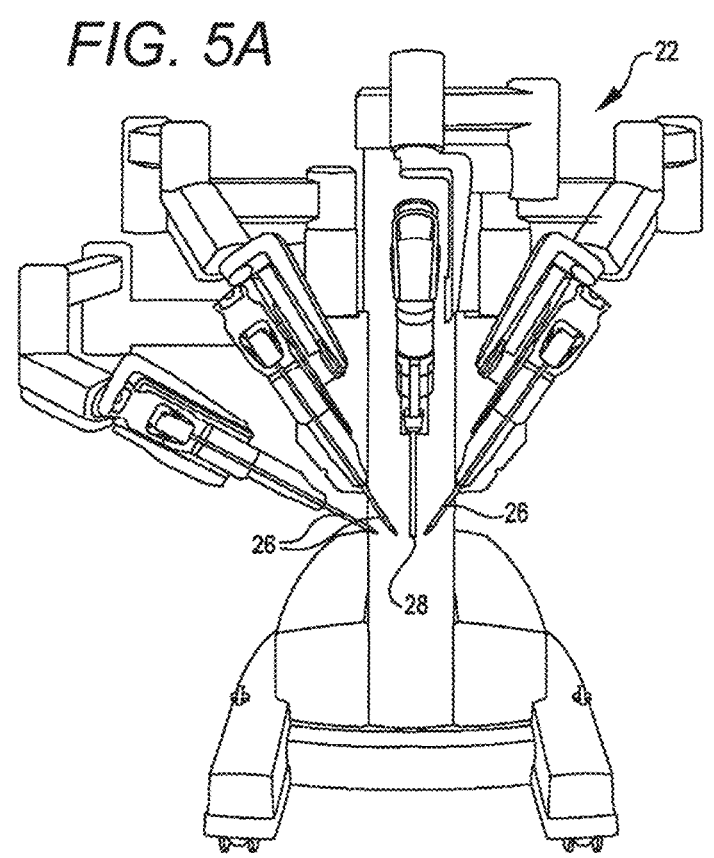
FIG. 5A is a front view of a patient side cart (surgical robot) of a robotic surgery system, in accordance with many embodiments.
Figure 5B:
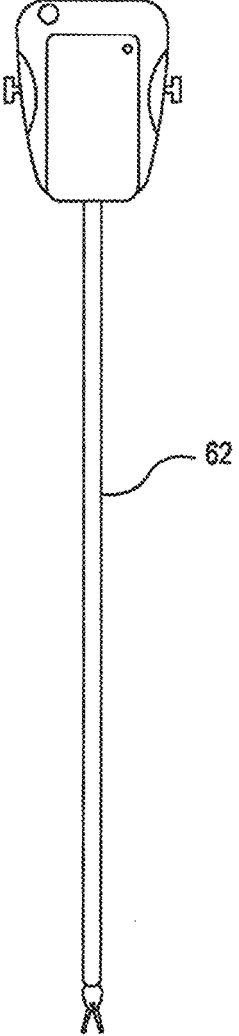
FIG. 5B is a front view of a robotic surgery tool, in accordance with many embodiments.

FIGS. 5A and 5B show a Patient Side Cart 22 and a surgical tool 62, respectively. The surgical tool 62 is an example of the surgical tools 26. The Patient Side Cart 22 shown provides for the manipulation of three surgical tools 26 and an imaging device 28, such as a stereoscopic endoscope used for the capture of images of the site of the procedure. Manipulation is provided by robotic mechanisms having a number of robotic joints. The imaging device 28 and the surgical tools 26 can be positioned and manipulated through incisions in the patient so that a kinematic remote center is maintained at the incision to minimize the size of the incision. Images of the surgical site can include images of the distal ends of the surgical tools 26 when they are positioned within the field-of-view of the imaging device 28.

Tissue Gripping End Effectors

Figure 6:
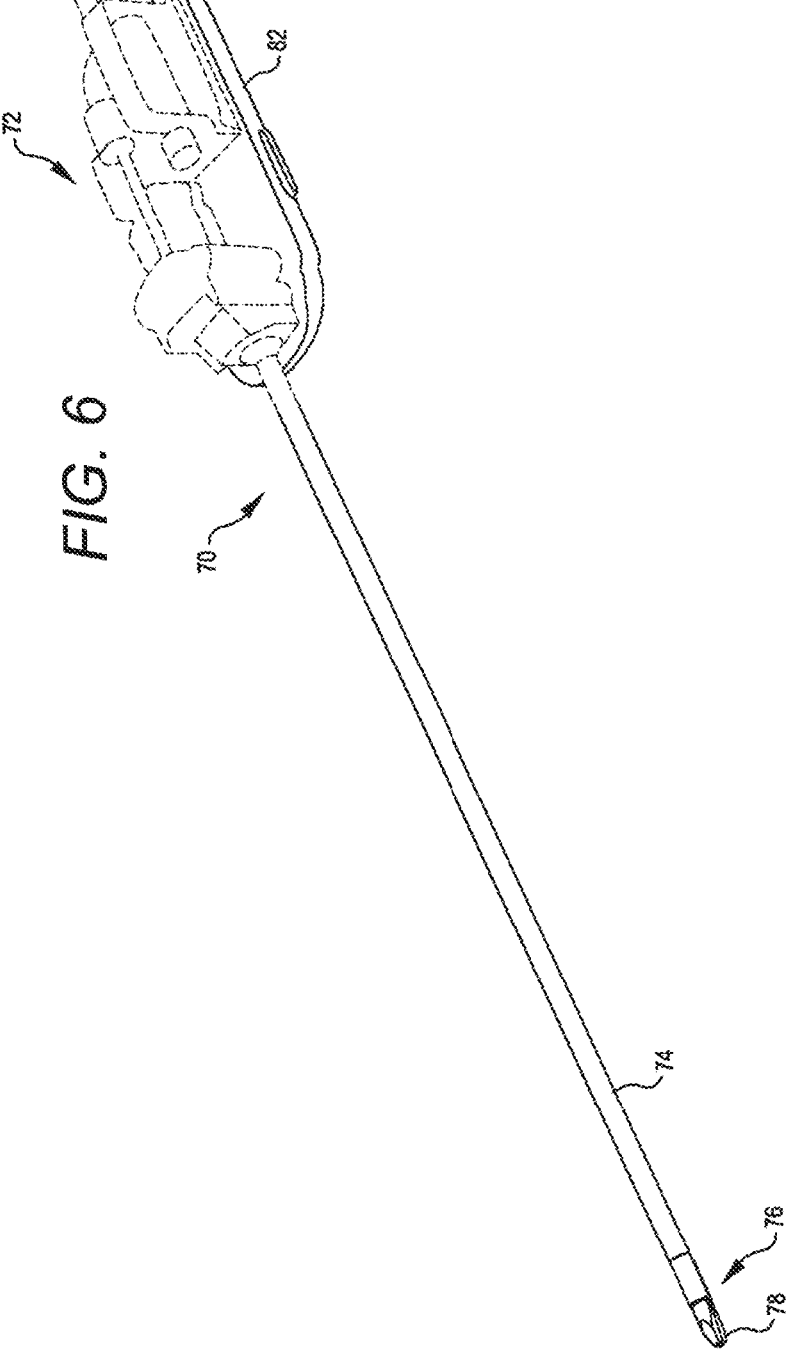
FIG. 6 is a perspective view of a robotic surgery tool that includes an end effector having opposed clamping jaws, in accordance with many embodiments.

FIG. 6 shows a surgical tool 70 that includes a proximal chassis 72, an instrument shaft 74, and a distal end effector 76 having a jaw 78 that can be articulated to grip a patient tissue. The proximal chassis includes input couplers that are configured to interface with and be driven by corresponding output couplers of the Patient Side Cart 22. The input couplers are drivingly coupled with the end effector 76.

Linear Stapling and Cutting Surgical Instruments

Figure 7:
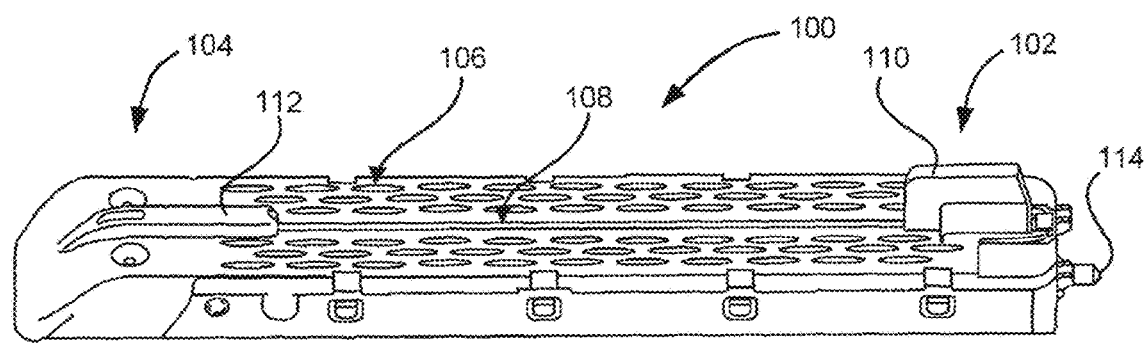
FIG. 7 is a perspective view of a demountably attachable cartridge of a linear stapling and cutting surgical instrument having six rows of staples, in accordance with many embodiments.
Figure 8:
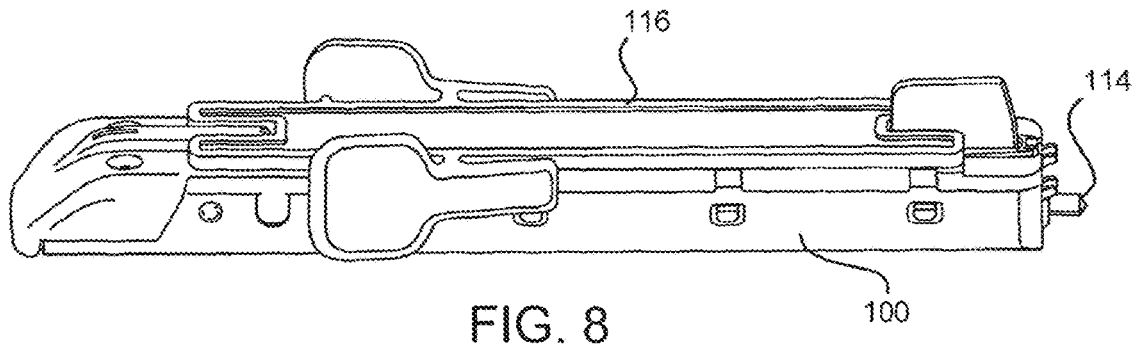
FIG. 8 is a perspective view of the cartridge of FIG. 7 and an attached staple retainer, in accordance with many embodiments.

FIG. 7 shows a demountably attachable cartridge 100 of a linear stapling and cutting surgical instrument, in accordance with many embodiments. The cartridge 100 can be used in a suitable surgical tool used in a suitable surgical system, such as in the surgical tools and surgical systems described herein (e.g., surgical system 10, surgery system 50). The cartridge 100 is configured to removably attach to a jaw of an end effector. The cartridge has a proximal end 102 that is attached to the jaw of the end effector and a distal end 104 disposed at a corresponding distal end of the jaw of the end effector. The cartridge 100 includes six rows of staple openings 106, a longitudinal slot 108, a proximal knife garage 110, a distal knife garage 112, and a rotational input 114. In many embodiments, a staple is disposed in each of the staple openings for deployment there from. The longitudinal slot 108 accommodates a cutting blade of a knife member (not shown) extending there from as the knife member is moved from the proximal knife garage 110 to the distal knife garage 112. In operation, the staples are deployed starting at the cartridge proximal end 102 and proceeding to the cartridge distal end 104. The cutting blade is moved to trail the stapling of the tissue to ensure that only fully stapled tissue is cut. FIG. 8 shows the cartridge 100 with an attached staple retainer 116, which is removed prior to using the cartridge 100.

Figure 9:
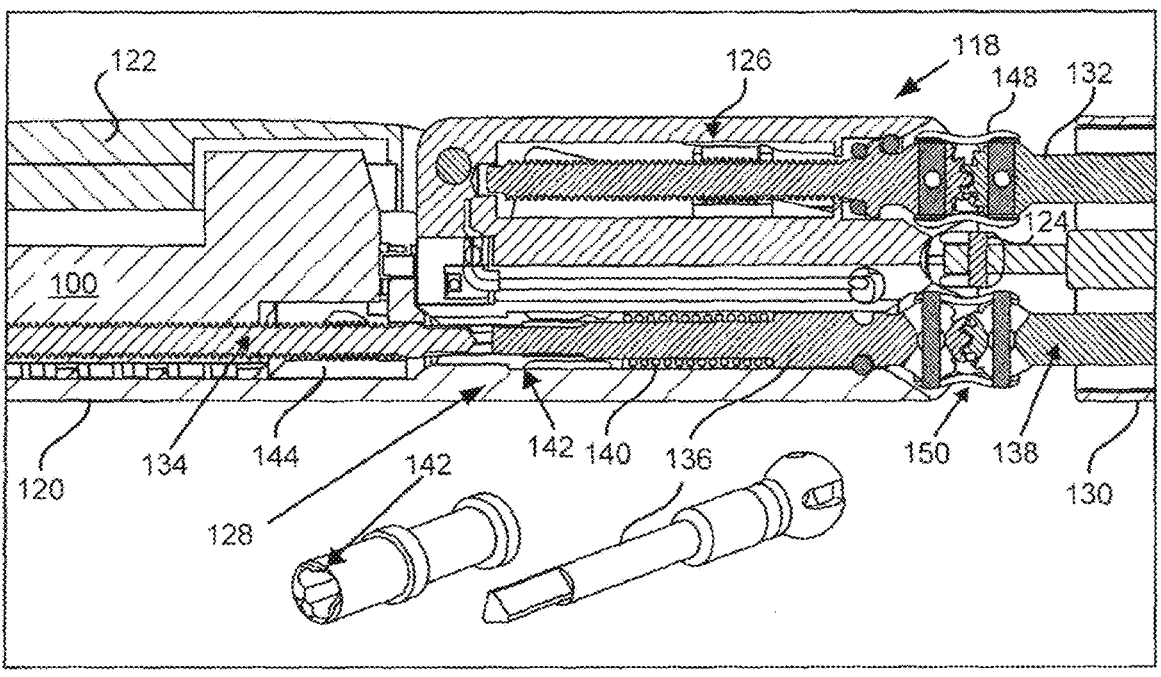
FIG. 9 is a cross-sectional view showing attachment details between the cartridge of FIG. 7 and an end effector assembly, in accordance with many embodiments.

FIG. 9 is a cross-sectional view showing details of the attachment of the cartridge 100 to an end effector 118, in accordance with many embodiments. The end effector 118 includes a lower jaw 120, an upper jaw 122, a two degree of freedom wrist 124, a rotationally-driven clamping mechanism 126, and a spring loaded coupling 128. The lower jaw 120 is configured to accommodate and support the cartridge 100, as well as position the cartridge 100 relative to the spring loaded coupling 128. The upper jaw 122 is pivotally coupled with the lower jaw 120 to articulate relative to the lower jaw 120 to clamp tissue. The upper jaw 122 includes staple forming recesses configured and positioned relative to the staple openings 106 to form the staples into a "B" shape upon deployment of the staples.

The two degree of freedom wrist 124 provides for attachment of the end effector 118 to an elongated instrument shaft 130 for articulation of the end effector 118 about two orthogonal axes relative to the instrument shaft 130. Details of a suitable two degree of freedom wrist that can be used are disclosed in U.S. Pat. No. 8,852,174, entitled "SURGICAL TOOL WITH A TWO DEGREE OF FREEDOM WRIST," filed Nov. 12, 2010, the full disclosure of which is hereby incorporated herein by reference.

The rotationally-driven clamping mechanism 126 actuates the upper jaw 122 relative to the lower jaw 120 to securely clamp tissue between the upper and lower jaws. The clamping mechanism 126 is rotationally driven by a first drive shaft 132 disposed internal to the instrument shaft 130. Details of a suitable rotationally-driven clamping mechanism that can be used are disclosed in U.S. Pat. No. 8,876,857, entitled "END EFFECTOR WITH REDUNDANT CLOSING MECHANISMS," filed Nov. 12, 2010, the full disclosure of which is hereby incorporated herein by reference.

The spring-loaded coupling 128 rotationally couples a lead screw 134 of the cartridge 100 with an extension shaft 136, which is driven by a second drive shaft 138 disposed internal to the instrument shaft 130. The spring-loaded coupling 128 includes a coil spring 140 and a coupling fitting 142. In the embodiment shown, the coupling fitting 142 employs a three-lobe spline receptacle that interfaces with three-sided external surfaces of the rotational input 114 and of the extension shaft 136. The spring-loaded coupling 142 accommodates angular misalignment of the three-lobe spline that might occur when the cartridge 100 is installed into the end effector 118. The spring-loaded coupling 142 fully engages the three-lobe spline when rotated into angular alignment. Rotation of the lead screw 134 is used to translate a drive member 144 of the cartridge 100 from its initial proximal position illustrated toward the distal end 104 of the cartridge 100. The resulting distal motion of the drive member 144 is used to deploy the staples and to distally advance a knife to cut the clamped tissue down the center of the rows of deployed staples.

The end effector 118 includes a first universal joint assembly 148 and a second universal joint assembly 150. The first universal joint assembly 148 rotationally couples the clamping mechanism 126 to the first drive shaft 132. The second universal joint assembly 150 rotationally couples the extension shaft 136 to the second drive shaft 138. Each of the first and second universal joint assemblies 148, 150 is configured to transmit torque through a range of angles suitable to the range of Pitch and Yaw of the end effector 118 relative to the instrument shaft 130. Details of a suitable universal joint assembly that can be used are disclosed in U.S. Publication No. 2011-0118708, entitled "DOUBLE UNIVERSAL JOINT," filed Nov. 12, 2010, the full disclosure of which is hereby incorporated herein by reference.

The first and second drive shafts 132, 138 are disposed offset to the centerline of the instrument shaft 130, which may be independently rotated. Details of a suitable drive mechanism that can be used to actuate the first and second drive shafts 132, 138 are disclosed in U.S. Pat. No. 8,640,788, entitled "MOTOR INTERFACE FOR PARALLEL DRIVE SHAFTS WITHIN AN INDEPENDENTLY ROTATING MEMBER," filed Nov. 12, 2010, the full disclosure of which is hereby incorporated herein by reference.

Cartridge Status and Presence Detection Methods

When an unfired cartridge 100 is mounted to the end effector 118, the drive member 144 is disposed at or near the proximal end of its range of possible positions along the lead screw 134 as illustrated in FIG. 9. Accordingly, it is not possible to advance the drive member 144 of an unfired cartridge 100 toward the proximal end 102 by more than a predictable amount, thereby limiting the amount of corresponding rotation of the second drive shaft 138. In contrast, when a fired cartridge 100 is mounted to the end effector 118, the drive member 144 is disposed at or near the distal end of its range of possible positions along the lead screw 134. Accordingly, it is possible to advance the drive member 144 of a fired cartridge 100 toward the proximal end much more than possible with an unfired cartridge 100, thereby permitting a substantially larger amount of corresponding rotation of the second drive shaft 138. And when no cartridge 100 is mounted to the end effector 118, the second drive shaft 138 can be rotated substantially freely. The limited possible travel of the drive member 144 of an unfired cartridge 100 can be used to verify the presence of an unfired cartridge 100 mounted to the end effector 118.

FIG. 10 lists acts of a method 200 for verifying the presence of an unfired surgical cartridge mounted to a surgical instrument, in accordance with many embodiments. The cartridge includes an input that is actuated in a firing direction to operate the cartridge. Any suitable surgical instrument that includes actuated cartridge mounted to the surgical instrument can be used to practice the method 200.

For example, suitable surgical systems and surgical instruments described herein can be used to practice the method 200.

In act 202, an actuation input that is limited to less than or equal to a predetermined magnitude is generated. The actuation input includes at least one of a torque or a force. In act 204, the actuation input is transferred to an output of the surgical instrument to attempt to actuate the output opposite to the firing direction by a predetermined amount. The output is drivingly coupled with the cartridge input when the cartridge is mounted to the surgical instrument. In act 206, a resulting actuation amount of the output is measured. In act 208, the resulting actuation amount of the output is compared with a threshold actuation amount. And in act 210, a determination is made that the cartridge is present and unfired when the resulting actuation amount of the output is less than the threshold actuation amount.

FIG. 11 lists optional acts that can be accomplished in the method 200, in accordance with many embodiments. In optional act 212, an electric current supplied to an electric motor used to generate the actuation input is limited, thereby serving to limit the actuation input that can be generated by the electric motor. In optional act 214, friction in a drive train used to transfer the actuation input to the output is measured, and the predetermined magnitude is set to be greater than the measured friction. In optional act 216, the predetermined magnitude is set to be less than a set percentage of a normal operating limit (e.g., torque limit, force limit) of the surgical instrument. For example, in many embodiments the predetermined magnitude is less than 40% of the normal operating limit. And in many embodiments, the predetermined magnitude is less than 20% of the normal operating limit. As a specific example, in a surgical instrument having a 100 mNm firing torque limit the predetermined magnitude can be set at 15 mNm. In optional act 218, the measuring of a resulting actuation amount of the output includes tracking the output of a sensor (e.g., a Hall sensor, an encoder) configured to track actuation of a drive train used to transfer the actuation input to the output. The actuation of the drive train can be tracked directly or indirectly (e.g., via tracking a drive source such as by tracking rotation of a motor drivingly coupled with the drive train). In optional act 220, the measuring of a resulting actuation amount of the output includes tracking movements of the output, and processing the tracked movements of the output to monitor for stalling of the attempted actuation of the output. In optional act 222, when stalling of the attempted actuation is detected, the generation of the actuation input is terminated.

The methods disclosed herein can be employed in any suitable application. For example, the methods disclosed herein can be employed in surgical instruments, manual or powered, hand-held or robotic, directly controlled or teleoperated, for open or minimally invasive (single or multiport) procedures.

Attempted Actuation Considerations

In many embodiments, the predetermined actuation (e.g., rotation) amount is selected to be greater than a maximum amount that may be needed to proximally drive the drive member 144 to the end of its possible proximal travel along the lead screw 134 and into engagement with the housing of the cartridge 100, thereby stalling any further rotation of the lead screw 134. The maximum rotation amount that may be needed depends on the range of possible starting positions of the drive member 144 relative to the end of its possible proximal travel along the lead screw 134, backlash in the drive train used to transfer the generated actuation torque to the lead screw 134, and compliance in the drive train arising from the transmitted torque. The compliance in the drive train can be reduced by setting the predetermined magnitude limit of the generated torque to be as low as practical while still being high enough to account for the frictional characteristics of the drive train. And the range of possible starting positions of the drive member 144 relative to the end of its possible proximal travel along the lead screw 134 can be reduced by suitable attention in the manufacture of the cartridge 100 to ensure that the drive member 144 is positioned as close to the end of its possible proximal travel along the lead screw 134 as possible (e.g., by adding a task in which the rotary input 114 is rotated opposite to the firing rotation direction as far as possible). Even when the drive member 144 is positioned at the end of its possible proximal travel along the lead screw 134, the use of the tri-lobe coupling 142 can result in a certain amount of offset of the drive member 144 from the end of its possible proximal travel along the lead screw 134 due to rotation of the rotary input 114 in the firing direction used to align the rotary input 114 with the coupling 142. In one exemplary embodiment, the maximum amount of rotation that may be needed is expected to be less than 1.5 turns of the rotary input 114.

Figure 12:
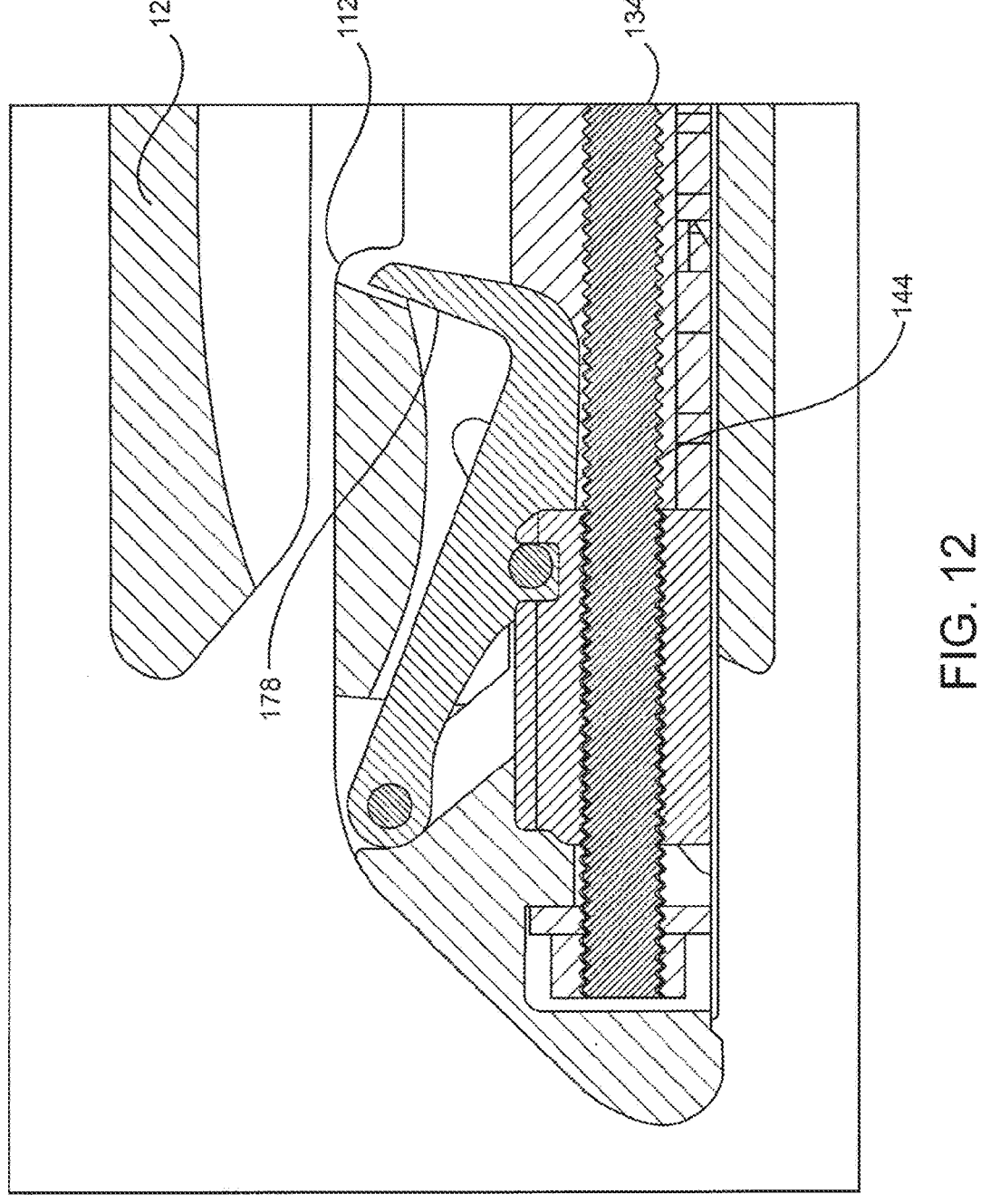
FIG. 12 illustrates an exemplary articulated knife configuration for a fired surgical cartridge.

In many embodiments, the predetermined rotation amount is also selected to be less than an amount of rotation that would result in exposure of the knife when applied to a surgical cartridge in a fired configuration. For example, FIG. 12 illustrates an exemplary articulated knife configuration for a fired surgical cartridge. As shown, the drive member 144 is disposed at the distal end of the lead screw 134, thereby shielding a cutting blade 178 of the knife member within the distal garage 112 of the cartridge 100. In the embodiment shown, the lead screw 134 can be rotated opposite to the firing direction by 2.9 turns before the cutting blade 178 is exposed. Accordingly, in an exemplary embodiment where the maximum amount of rotation that may be needed to stall rotation of the attempted rotation is 1.5 turns and the amount of rotation that would result in exposure of the cutting blade of the knife is 2.9 turns, the selected predetermined rotation amount can be between these two numbers, for example, 2.0 turns. After the lead screw 134 is driven (opposite the firing direction) the selected predetermined rotation amount to detect a fired cartridge, the lead screw 134 is driven forward the same selected predetermined rotation amount to restore the knife to the original, fully fired position. This is done to prevent driving the knife out of the garage after successively inserting fired cartridges.

Cartridge Status and Presence Detection Systems

Figure 13:
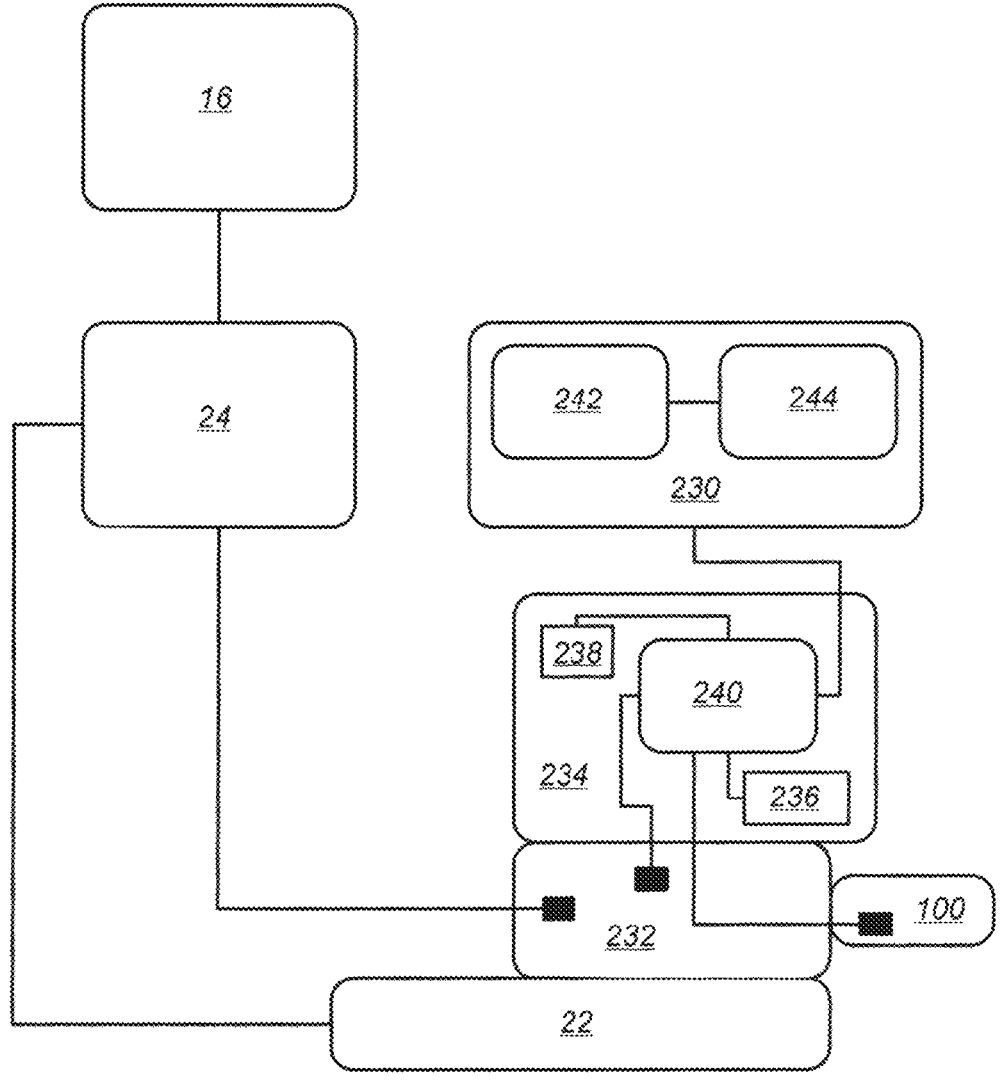
FIG. 13 a simplified schematic diagram providing a high level view of components related to implementing verification of the presence of an unfired surgical cartridge mounted to a surgical instrument of a robotic surgical system, in accordance with many embodiments.

FIG. 13 a simplified schematic diagram providing a high level view of components related to implementing verification of the presence of an unfired surgical cartridge mounted to a surgical instrument of a robotic surgical system (e.g., surgical system 10, surgery system 50), in accordance with many embodiments. The robotic surgical system includes the Surgeon's Console 16, the Electronics Cart 24, the Patient Side Cart 22, an instrument control box (ICB) 230, a surgical instrument 232, the surgical cartridge 100, and a motor pack 234.

The surgical instrument 232 is configured to receive and support the surgical cartridge 100. The surgical instrument 232 includes a rotary output. The surgical cartridge 100 includes an input that is rotated in a firing direction to operate the surgical cartridge 100. The cartridge input is drivingly coupled with the rotary output when the surgical cartridge 100 is mounted to the surgical instrument 232. The motor pack 234 is mounted to the surgical instrument 232 and includes a motor 236 that is drivingly coupled with the rotary output of the surgical instrument 232. The motor pack 234 includes a sensor 238 (e.g., position sensor, velocity sensor, acceleration sensor) configured to measure rotation of the rotary output of the surgical instrument 232. And the motor pack 234 includes a local processor 240 that is communicatively coupled with the ICB 230, the sensor 238, and the motor 236. In many embodiments, the sensor measures rotations of the rotary output of the surgical instrument 232 by measuring rotations of the motor 236.

The ICB 230 is communicatively coupled with the sensor 238 and the motor 236 through the motor pack local processor 240. The ICB 230 includes a processor 242 and a tangible storage medium 244. The tangible storage medium 244 contains instructions that when executed cause the processor 242 to control the motor 236 such that the motor 236 generates an actuation torque that is less than or equal to a predetermined magnitude (e.g., less than 40% of a normal operating torque limit of the surgical instrument 232—including the surgical cartridge 100, less than 20% of the normal operating torque limit). In many embodiments, an electrical current supplied to the motor 236 is limited to limit the amount of possible torque generated by the motor 236. The generated actuation torque is transferred to the surgical instrument rotary output to attempt to rotate the rotary output opposite to the firing direction of the surgical cartridge 100 through a predetermined rotation amount. The ICB processor 242 compares a resulting rotation of the rotary output with a threshold rotation amount and determines that the cartridge 100 is present and unfired when the resulting rotation of the rotary output is less than the threshold rotation amount.

In many embodiments, the sensor 238 can be a position sensor and include a Hall sensor. The ICB processor 242 can count Hall sensor counts and compare the Hall sensor counts to a predetermined number to determine if the resulting rotation of the rotary output, or a derived quality thereof, of the surgical instrument 232 is less than the threshold amount (e.g., a predetermined number of rotations or derived velocity value). Other suitable position sensors can also be used. For example, the position sensor can include an encoder.

In many embodiments, the sensor 238 can be a velocity sensor and include, for example, an inductive velocity sensor or a tachometer. The ICB processor 242 can determined if the output, or a derived quality thereof, of the velocity sensor is less than a threshold amount (e.g., a predetermined velocity value or derived position value).

In many embodiments, the sensor 238 can be an acceleration sensor and include, for example, an accelerometer. The ICB processor 242 can determined if the output, or a derived quality thereof, of the acceleration sensor is less than a threshold amount (e.g., a predetermined acceleration value or derived position value).

The ICB processor 242 is configured to monitor for stalling of the attempted rotation of the rotary output. The ICB processor 242 tracks rotations of the rotary output and processes the tracked rotations to detect when the rotary output rotates less than a minimum amount in a predetermined time period.

In many embodiments, the surgical cartridge 100 includes an articulated knife. The predetermined rotation amount can be selected to be less than the rotation that would result in exposure of the knife when applied to the surgical instrument in a fired configuration. The cartridge can include staples that are deployed into clamped tissue when the cartridge is operated. The articulated knife can be configured to cut the clamped tissue between rows of the deployed staples. The cartridge can be configured to seal a vessel and include an articulated knife configured to cut the sealed vessel.

The control systems described herein used to verify the presence of an unfired surgical cartridge mounted to a surgical instrument can be employed in any suitable surgical system described herein. And the methods described herein can be practiced using any of the suitable surgical systems, surgical instruments, and/or surgical cartridges described herein.

Other variations are within the spirit of the present invention. Thus, while the invention is susceptible to various modifications and alternative constructions, certain illustrated embodiments thereof are shown in the drawings and have been described above in detail. It should be understood, however, that there is no intention to limit the invention to the specific form or forms disclosed, but on the contrary, the intention is to cover all modifications, alternative constructions, and equivalents falling within the spirit and scope of the invention, as defined in the appended claims.

The term "force" is to be construed as encompassing both force and torque (especially in the context of the following claims), unless otherwise indicated herein or clearly contradicted by context. The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

What is claimed is:

1. A method of detecting that a surgical instrument does not have a surgical cartridge in a staple-unfired condition mounted to the surgical instrument, the surgical instrument including an actuation output that is actuated in a first direction to fire at least one staple in the surgical cartridge in the staple-unfired condition when the surgical cartridge in the staple-unfired condition is mounted to the surgical instrument, the method comprising:

commanding a movement of the actuation output in a second direction, the second direction being opposite to the first direction;

detecting that an actuation amount of the actuation output as a result of the commanded movement of the actuation output in the second direction is at or above a threshold actuation amount; and in response to detecting that the actuation amount of the actuation output as a result of the commanded movement of the actuation output in the second direction is at or above the threshold actuation amount, determining that the surgical instrument does not have the surgical cartridge in the staple-unfired condition mounted to the surgical instrument.

2. The method of claim 1, wherein commanding the movement of the actuation output in the second direction comprises generating an actuation input to the surgical instrument that is subject to a torque limit or force limit.

3. The method of claim 2, wherein generating the actuation input that is subject to the torque limit or force limit comprises limiting an electric current supplied to an electric motor used to generate the actuation input to the surgical instrument.

4. The method of claim 2, further comprising:

terminating the actuation input in response to an exceedance of the torque limit or force limit;

measuring an amount of movement of the actuation output in the second direction achieved; and comparing the amount of movement of the actuation output in the second direction achieved with the commanded movement of the actuation output in the second direction.

5. The method of claim 4, wherein measuring the amount of movement of the actuation output in the second direction achieved comprises interrogating a sensor tracking a position of an element of a drive train used to transfer the actuation input to the surgical instrument.

6. The method of claim 2, further comprising:

measuring a friction in a drive train used to transfer the actuation input to the surgical instrument; and configuring the torque limit or force limit to be sufficient to overcome the measured friction.

7. The method of claim 2, further comprising configuring the torque limit or force limit to be less than a normal operating limit of the surgical instrument.

8. The method of claim 7, wherein configuring the torque limit or force limit to be less than a normal operating limit of the surgical instrument comprises configuring the torque limit or force limit to be less than 20% of the normal operating limit.

9. The method of claim 1, wherein the commanded movement of the actuation output in the second direction is less than an amount of movement of the actuation output that would be sufficient to move a knife of the surgical cartridge in a staple-fired condition mounted to the surgical instrument from a stowed position to an exposed position.

10. A surgical instrument comprising:

an actuation output;

an end effector configured to receive and support a surgical cartridge, the surgical cartridge including an input that is drivingly coupled with the actuation output when the surgical cartridge is mounted to the end effector, the actuation output being actuated in a first direction to fire at least one staple in the surgical cartridge;

a drive source drivingly coupled with the actuation output;

a sensor that generates an output indicative of movement of the actuation output; and a controller communicatively coupled with the sensor and the drive source, the controller comprising a processor and a tangible storage medium containing instructions that when executed cause the processor to:

command a movement of the actuation output in a second direction, the second direction being opposite to the first direction;

detect whether an actuation amount of the actuation output as a result of the commanded movement of the actuation output in the second direction is at or above a threshold actuation amount; and in response to detecting the actuation amount of the actuation output as a result of the commanded movement of the actuation output in the second direction being at or above the threshold actuation amount, determine that the surgical instrument does not have the surgical cartridge in a staple-unfired condition mounted to the surgical instrument.

11. The surgical instrument of claim 10, wherein:

the surgical cartridge comprises an articulated knife; and the commanded movement of the actuation output in the second direction is less than an amount of movement that would result in exposure of the articulated knife when applied to the surgical cartridge in a staple-fired condition.

12. The surgical instrument of claim 10, wherein the surgical cartridge comprises:

a plurality of staples that are deployed into a clamped tissue when the at least one staple in the surgical cartridge is fired; and an articulated knife configured to cut the clamped tissue between rows of the deployed staples.

13. The surgical instrument of claim 10, wherein the surgical cartridge is configured to seal a vessel and includes an articulated knife configured to cut the sealed vessel.

14. The surgical instrument of claim 10, wherein the instructions, when executed, further cause the processor to:

terminate the movement of the actuation output in response to an exceedance of a torque limit or force limit;

measure an amount of movement of the actuation output in the second direction achieved; and compare the amount of movement of the actuation output in the second direction achieved with the commanded movement of the actuation output in the second direction.

* * * * *